United States Patent
Niu et al.

(10) Patent No.: US 7,755,038 B2
(45) Date of Patent: *Jul. 13, 2010

(54) NANOSTRUCTURED THIN FILMS AND THEIR USES

(75) Inventors: Chunming Niu, Palo Alto, CA (US); Robert Hugh Daniels, Mountain View, CA (US); Robert S. Dubrow, San Carlos, CA (US); Jay L. Goldman, Mountain View, CA (US)

(73) Assignee: Nanosys, Inc., Palo Alto, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/121,008

(22) Filed: May 15, 2008

(65) Prior Publication Data

US 2009/0124034 A1     May 14, 2009

Related U.S. Application Data

(63) Continuation of application No. 11/226,075, filed on Sep. 14, 2005, now Pat. No. 7,391,018.

(60) Provisional application No. 60/611,116, filed on Sep. 17, 2004.

(51) Int. Cl.
    *H01J 49/04* (2006.01)

(52) U.S. Cl. .................. 250/288; 428/650; 428/651; 977/701

(58) Field of Classification Search .................. None
    See application file for complete search history.

(56) References Cited

U.S. PATENT DOCUMENTS

| 4,728,796 | A | 3/1988 | Brown |
| 4,987,007 | A | 1/1991 | Wagal et al. |
| 4,988,879 | A | 1/1991 | Zare et al. |
| 5,260,571 | A | 11/1993 | Cottrell et al. |
| 5,382,793 | A | 1/1995 | Weinberger et al. |
| 5,389,786 | A | 2/1995 | Itoh et al. |

(Continued)

FOREIGN PATENT DOCUMENTS

WO     2004099068     11/2004

OTHER PUBLICATIONS

Alivisatos A.P. "Semiconductor clusters nanocrystals and quantum dots" Science (1996) 271:933-937.

(Continued)

*Primary Examiner*—Jack I Berman
(74) *Attorney, Agent, or Firm*—Andrew L. Filler

(57) ABSTRACT

The present invention generally discloses the use of a nanostructured non-silicon thin film (such as an alumina or aluminum thin film) on a supporting substrate which is subsequently coated with an active layer of a material such as silicon or tungsten. The base, underlying non-silicon material generates enhanced surface area while the active layer assists in incorporating and transferring energy to one or more analytes adsorbed on the active layer when irradiated with a laser during laser desorption of the analyte(s). The present invention provides substrate surfaces that can be produced by relatively straightforward and inexpensive manufacturing processes and which can be used for a variety of applications such as mass spectrometry, hydrophobic or hydrophilic coatings, medical device applications, electronics, catalysis, protection, data storage, optics, and sensors.

12 Claims, 9 Drawing Sheets

U.S. PATENT DOCUMENTS

| | | | |
|---|---|---|---|
| 5,552,272 | A | 9/1996 | Bogart |
| 5,580,733 | A | 12/1996 | Levis et al. |
| 5,589,685 | A | 12/1996 | Wu et al. |
| 5,719,060 | A | 2/1998 | Hutchens et al. |
| 5,770,272 | A | 6/1998 | Biemann et al. |
| 5,777,324 | A | 7/1998 | Hillenkamp |
| 5,828,063 | A | 10/1998 | Koster et al. |
| 5,854,486 | A | 12/1998 | Dreyfus |
| 5,882,496 | A | 3/1999 | Northrup et al. |
| 5,894,063 | A | 4/1999 | Hutchens et al. |
| 5,919,712 | A | 7/1999 | Herron et al. |
| 6,057,543 | A | 5/2000 | Vestal et al. |
| 6,071,610 | A | 6/2000 | Jarrell et al. |
| 6,207,229 | B1 | 3/2001 | Bawendi et al. |
| 6,288,390 | B1 | 9/2001 | Siuzdak et al. |
| 6,322,901 | B1 | 11/2001 | Bawendi et al. |
| 6,332,363 | B1 | 12/2001 | Molloy et al. |
| 6,399,177 | B1 | 6/2002 | Fonash et al. |
| 6,454,924 | B2 | 9/2002 | Jedrzejewski et al. |
| 6,652,669 | B1 | 11/2003 | Reihs et al. |
| 7,122,790 | B2 | 10/2006 | Fonash et al. |
| 7,391,018 | B2 * | 6/2008 | Niu et al. .................... 250/288 |
| 2002/0048531 | A1 | 4/2002 | Fonash et al. |
| 2002/0187312 | A1 | 12/2002 | Fonash et al. |
| 2002/0193950 | A1 | 12/2002 | Gavin et al. |
| 2003/0057106 | A1 | 3/2003 | Shen et al. |
| 2004/0094705 | A1 | 5/2004 | Wood et al. |
| 2004/0178390 | A1 | 9/2004 | Whiteford et al. |
| 2004/0250950 | A1 | 12/2004 | Dubrow |
| 2005/0181195 | A1 | 8/2005 | Dubrow |
| 2005/0219788 | A1 | 10/2005 | Chow |
| 2005/0221072 | A1 | 10/2005 | Dubrow |

OTHER PUBLICATIONS

Barber M. et al. "Fast atom bombardment of solids as an ion source in mass spectrometry" Nature (1981) 293:270-275.

Brown K.N. et al. "Mass spectrometry analysis of ubiquitin on deposited column/void network silicon thin films" Nat'l Nanofab Users Net (Publication date unknown).

Cui Y. et al. "Nanowire nanosensors for highly sensitive and selective detection of biological and chemical species" Science (2001) 293;1289-1292.

Cui Y. et al. "Functional nanoscale electronic devices assembled using silicon nanowire building blocks" Science (2001) 291:851-853.

Cuiffi J.D. et al. "Desorption-ionization mass spectrometry using deposited nanostructured silicon films" Anal. Chem. (2001) 73:1292-1295.

Dreve S. et al. "Nanostructured 'brush-type' thin-film covered with a silver layer" J. Optoelec. Adv. Mater. (2004) 6 (2):477-479.

Duan X. et al. "Single-nanowire electrically driven lasers" Nature (2003) 421:241-245.

Greene L.E. et al. "Low-Temperature Wafer-Sacle Production of ZnO Nanowire Arrays" Angew. Chem. Int. Ed. (2003) 42:3031-3034.

Hahm J. et al. "Direct ultrasensitive electrical detection of DNA and DNA sequence variations using nanowire nanosensors" Nano Lett. (2004) 4:51-54.

Hillenkamp F. et al. "Matrix-assisted laser desorption/ionization mass spectrometry of biopolymers" Anal. Chem. (1991) 63 A1193-A1202.

Hrubowchak D.M. et al. "Detection of biomolecules on surfaces using ion-beam-induced desorption and multiphoton resonance ionization" Anal. Chem. (1991) 63:1947-1953.

Huang Y. et al. "Integrated optoelectonics assembled from semiconductor nanowires" Abstracts of Papers of the American Chemical Society (2002) 224:U308.

Karas M. et al. "Laser desorption ionization of proteins with molecular masses exceeding 10000 daltons" Anal. Chem. (1988) 60:2299-2301.

Kruse R.A. et al. "Experimental factors controlling analyte ion generation in laser desorption/ionization mass spectrometry on porous silicon" Anal. Chem. (2001) 73:3639-3645.

MacFarlane R.D. et al. "Californium-252 plasma desorption mass spectroscopy" Science (1976) 191:920-925.

Murray C.B. et al. "Synthesis and characterization of nearly monodisperse CdE (E = sulfur selenium tellurium) semiconductor nanocrystallites" J. Am. Chem. Soc. (1993) 115:8706-8715.

Palibroda E. et al. "Aluminum porous oxide growth. On the electric conductivity of the barrier layer" Thin Solid Films (1995) 256:101-105.

Peng X. et al. "Epitaxial growth of highly luminescent CdSe/CdS Core/Shell nanocrystals with photostability and electronic accessibility" J. Am. Chem. Soc. (1997) 30:7019-7029.

Posthumus M.A. et al. "Laser desorption-mass spectrometry of polar nonvolatile bio-organic molecules" Anal. Chem. (1978) 50:985-991.

Ross C.A. et al. "Nanostructured surfaces with long-range order for controlled self-assembly" NSF Nanoscale Sci and Eng. Grantees Conf. (2003).

Shen Z. et al. "Porous silicon as a versatile platform for laser desorption/ionization mass spectrometry" Anal Chem. (2001) 73:612-619.

Tadanaga K. et al. "Formation process of super-water-repellent Al2O3 coating films with high transparency by the Sol-Gel method" J. Am. Chem. Soc. (1997) 80(12):3213-3216.

Thomas J.J. et al. "Desorption/ionization on silicon (DIOS): a diverse mass spectrometry platform for protein characterization" Proc. Natl Acad. Sci. (2001) 98:4932-4937.

Trauger S.A. et al. "High sensitivity and analyte capture with desorption/ionization mass spectrometry oon silylated porous silicon" Anal. Chem. (2004) 76:4484-4489.

Wang S.L. et al. "Studies of silicon nitride (Si3N4) using laser ablation mass spectrometry" Appl. Surf. Sci (1996) 93:205-210.

Zhan Q. et al. "Laser desorption substrate effects" J. Am. Soc. Mass. Spectr. (1997) 8:525-531.

Zhou X.T. et al. "Silicon nanowires as chemical sensors" Chem. Phys. Lett. (2003) 369:220-224.

* cited by examiner

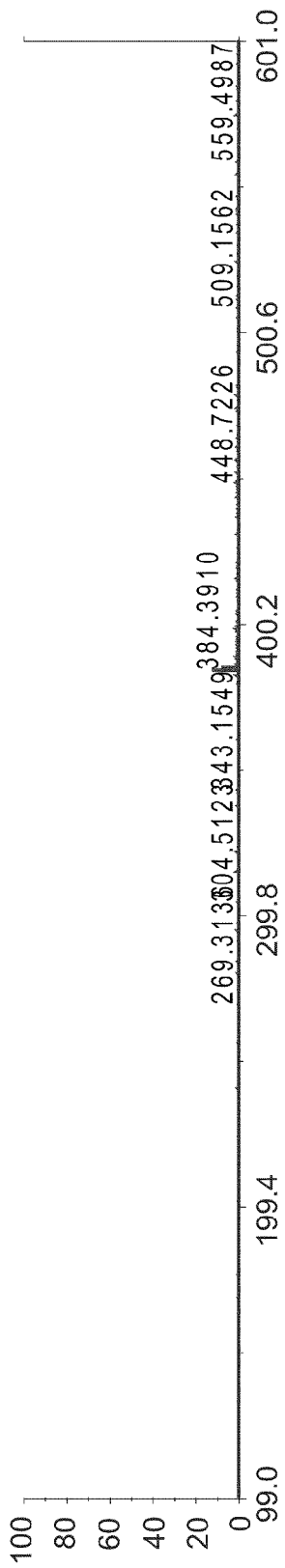
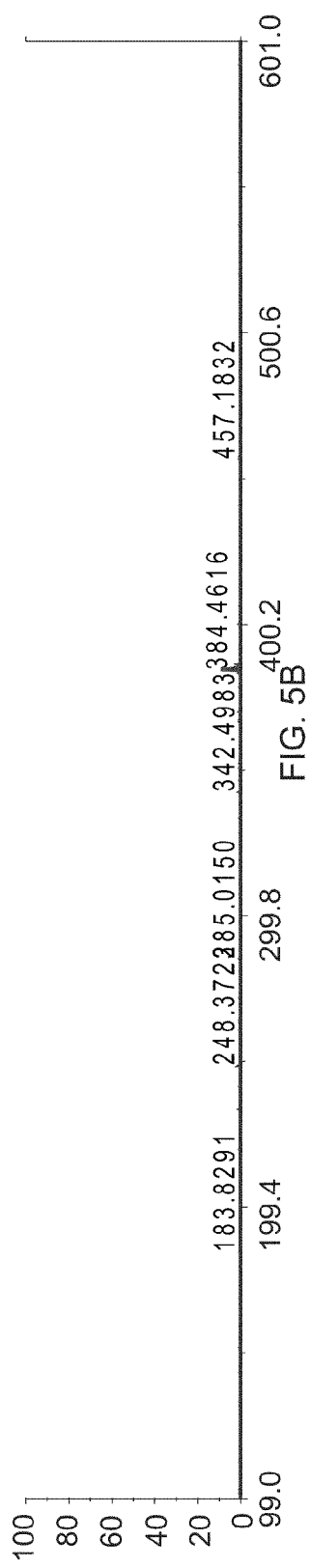
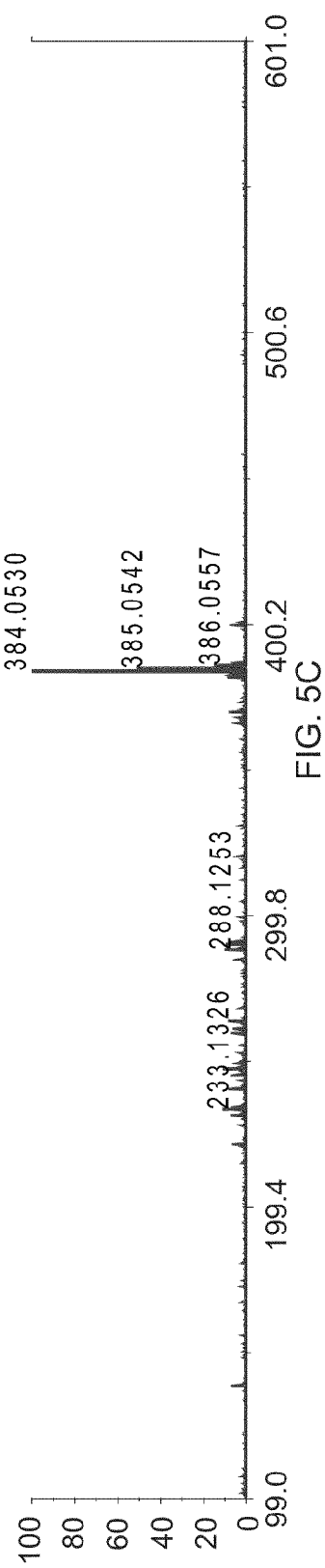
FIG. 5A
FIG. 5B
FIG. 5C

NANOSTRUCTURED THIN FILMS AND THEIR USES

CROSS-REFERENCE TO RELATED APPLICATIONS

This application is a continuation of U.S. patent application Ser. No. 11/226,075, filed Sep. 14, 2005, now U.S. Pat. No. 7,391,018 which application claims the benefit of U.S. Provisional Patent Application No. 60/611,116, filed Sep. 17, 2004, which is incorporated in its entirety herein.

STATEMENT REGARDING FEDERALLY SPONSORED RESEARCH

Portions of this invention may have been made with United States Government support under the Department of Health and Human Services, National Institutes of Health, National Human Genome Research Institute grant number 1 R43 HG003480-01. As such, the United States Government may have certain rights in the invention.

FIELD OF THE INVENTION

The present invention relates primarily to the field of nanotechnology. More specifically, the invention pertains to nanostructured thin films and coatings and their uses in, e.g., high surface area applications such as mass spectrometry, as superhydrophobic coatings, as anti-bifouling coatings, as surfaces to promote cell attachment, differentiation and proliferation, etc.

BACKGROUND OF THE INVENTION

Nanotechnology has been heralded as the next major technological leap, in that it is prophesied to yield a variety of substantial advantages in terms of material characteristics, including electronic, optical and structural characteristics. Nanostructured materials as thin films and coatings possess unique properties due to both size and interface effects. Nanostructured materials are generally a broad class of materials, with microstructures modulated in zero to three dimensions on length scales typically less than about 500 nm, for example, less than about 200 nm, e.g., less than about 100 nm. Nanostructured materials find many applications in areas such as electronics, mass spectrometry, catalysis, protection, data storage, optics, and sensors. Nanostructured films and coatings have many advantages over conventional thin films including high surface area, increased hydrophobicity, increased adhesion, and other similar properties.

One particularly interesting use of nanostructured films and coatings is in mass spectrometry applications. Generally speaking, in mass spectrometry, a substance is bombarded with an electron beam having sufficient energy to fragment the molecule. The positive fragments which are produced (cations and radical cations) are accelerated in a vacuum through a magnetic field and are sorted on the basis of mass-to-charge (m/z) ratio in a mass analyzer. Since the bulk of the ions produced in the mass spectrometer carry a unit positive charge, the value m/z is equivalent to the molecular weight of the fragment. Modern advances in mass spectrometry often address problems regarding the handling of liquid or solid samples. As ions are actually analyzed in the vacuum of the mass spectrometer, arguably the most important reaction is the one that converts analytes of interest into gas-phase ions. Historically, the most commonly used ionization processes (for example, electron ionization) occur in two discrete steps: a sample which is adsorbed on a surface of a substrate is first volatilized and then ionized.

The past two decades have seen the development of new ionization techniques for the analysis of non-volatile and thermally labile compounds: Electrospray ionization (ESI) and matrix-assisted desorption/ionization (MALDI). ESI allows for large, non-volatile molecules to be analyzed directly from the liquid phase. Rather than using an electron beam to ionize a sample as with ESI, MALDI ionizes a sample by pulsed laser irradiation of the sample. The sample is co-crystallized with a solid matrix that can absorb the wavelength of light emitted by the laser. Usually the sample and matrix are mixed on a substrate and inserted into the mass spectrometer instrument, and after irradiation the gas-phase ions that are formed are directed toward the mass analyzer. The broad success of matrix-assisted laser desorption/ionization (MALDI) is related to the ability of the matrix to incorporate and transfer energy to the sample. Barber, et al., Nature 293, 270-275 (1981); Karas, et al., Anal. Chem. 60, 2299-2301 (1988); Macfarlane, et al., Science 191, 920-925 (1976); Hillenkamp, et al., Anal. Chem. 63, A1193-A1202 (1991)).

However, one of the drawbacks of MALDI is the presence of the matrix, which facilitates ionization, but also causes a large degree of chemical noise to be observed at m/z ratios below about 700 Daltons (e.g., for low molecular weight samples). As a result, samples with low molecular weights are usually difficult to analyze with MALDI. Recent variations of MALDI have involved direct desorption/ionization without a matrix and have potential for enabling the analyses of low molecular weight compounds. In particular, the desorption/ionization on porous silicon (DIOS) and silicon continuous or columnar thin films has been used as an alternative to MALDI, see, e.g., Siuzdak et al. U.S. Pat. No. 6,288,390; Fonash et al. U.S. Patent Application No. 20020048531 filed Dec. 19, 2000; Thomas, J. J., Shen, Z., Crowell, J. E., Finn, M. G. & Siuzdak, G., "Desporption/ionization on silicon (DIOS): a diverse mass spectrometry platform for protein characterization," Proc. Natl Acad. 98:4932-4937 (2001); Shen, Z., et al., "Porous silicon as a versatile platform for laser desorption/ionization mass spectrometry," Anal Chem. 73:612-619 (2001); Cuiffi, et al., "Desorption-ionization mass spectrometry using deposited nanostructured silicon films," Anal, Chem. 73:1292-1295 (2001); and, Kruse, et al., "Experimental factors controlling analyte ion generation in laser desorption/ionization mass spectrometry on porous silicon," Anal. Chem. 73:3639-3645 (2001). These methods typically use porous silicon or etched silicon columnar structures to trap analytes deposited on the surface, and laser irradiation to vaporize and ionize them. Most of these demonstrated applications to date have been based on the porous silicon material produced by electrochemically etching a wafer or deposited film of silicon.

Silicon nanowires have been the subject of extensive research in electronics, photonics, optoelectronics, sensing, and other novel device applications. See, e.g., Cui, et al., "Nanowire nanosensors for highly sensitive and selective detection of biological and chemical species," Science 293; 1289-1292 (2001); Cui, et al., "Functional nanoscale electronic devices assembled using silicon nanowire building blocks," Science 291:851-853 (2001); Huang, et al., "Integrated optoelectronics assembled from semiconductor nanowires," Abstracts of Papers of the American Chemical Society 224:U308 (2002); Zhou, et al., "Silicon nanowires as chemical sensors," Chem. Phys. Lett. 369:220-224 (2003); Duan, et al., "Single-nanowire electrically driven lasers,"

*Nature* 421:241-245 (2003); Hahm, et al., "Direct ultrasensitive electrical detection of DNA and DNA sequence variations using nanowire nanosensors," *Nano Lett.* 4:51-54 (2004). Silicon nanowires appear to be an ideal platform for surface-based mass spectrometry. In contrast to porous silicon, silicon nanowires are catalyzed and grown on the surface of a substrate and their physical dimensions, composition, density, and position can be precisely controlled at the nanoscale level, thus offering even greater potential for designing mass spectrometry active surfaces. See, e.g., U.S. Ser. No. 60/468,390 filed May 6, 2003, U.S. Ser. No. 60/468,606 filed May 5, 2003, and U.S. Ser. No. 10/792,402 filed Mar. 2, 2004, all three entitled "Nanofiber Surfaces for Use in Enhanced Surface Area Applications", the entire contents of which are incorporated by reference herein. However, the use of silicon nanowires as substrate surfaces may pose some challenges in terms of manufacturing such surfaces reproducibly for large-scale commercial production.

It would be beneficial to have a direct laser desorption/ionization technique that eliminates the need for matrix compounds, is reliable and relatively inexpensive to implement, and can be used in biomolecular and other analyses with standard MALDI (and other) mass spectrometer instruments. The present invention provides unique nanostructured thin film surfaces to generate high surface area substrates for matrix-free MALDI and other applications as well. By eliminating background peaks of interfering matrix compounds, good analyses of both low and high-molecular weight compounds such as small molecules, proteins, peptides, oligonucleotides, drugs, pesticides, carbohydrates, fatty acids and the like can be produced more quickly and reliably.

SUMMARY OF THE INVENTION

The present invention generally discloses the use of a nanostructured non-silicon thin film (such as an alumina or aluminum thin film) on a supporting substrate which is subsequently coated with an active layer of a second material (e.g., silicon, tungsten, etc.). The base underlying non-silicon material generates enhanced surface area while the active layer assists in incorporating and transferring energy to one or more analytes adsorbed on the active layer when irradiated with a laser during laser desorption of the analyte(s). The present invention provides substrate surfaces that can be produced by relatively straightforward and inexpensive manufacturing processes. The nanopatterned thin film produced by the methods of the present invention has characteristics of high uniformity over a relatively large area, strong adhesion to the underlying substrate, resistance to scratching, and can be easily applied onto large substrate materials. The nanostructured film may be used as a base layer for increasing the surface area of a substrate, e.g., for matrix-free mass spectrometry applications, for making a substrate surface superhydrophilic or superhydrophobic, for modifying the optical properties of a substrate, and/or for developing highly efficient catalytic surfaces, e.g., for the growth of nanofibers or other nanostructured components thereon.

In a first exemplary aspect of the invention, a device is disclosed which generally comprises a supporting substrate, a first layer of a nanostructured coating, and a second layer of an active coating. The supporting substrate can take a variety of forms such as a semiconductor wafer, a sheet of glass or quartz, a sheet of metal, a piece of ceramic or plastic. The first layer of nanostructured coating can comprise, for example, elongated or plate-like grains with at least one dimension less than about 0.2 µm. The long axis of plate-like grains may be oriented substantially perpendicular to a surface of the supporting substrate. In one aspect of the invention, the first layer of nanostructured coating comprises an insulating inorganic material such as a native oxide layer or a deposited oxide or nitride layer. The insulating inorganic material may also be formed form a deposited metal layer. For example, the insulating inorganic material may be selected from the group of materials including alumina ($Al_2O_3$), aluminum (Al), $SiO_2$, $ZrO_2$, $HfO_2$, a hydrous form of these oxides, a compound oxide such as $SiTiO_3$, $BaTiO_3$ $PbZrO_4$ or a silicate.

In one aspect of the invention, the active coating layer comprises a semiconductor which absorbs light energy such as IR, red, green, blue and/or UV laser light energy. The semiconductor may be selected from Group IV semiconductors including Si, Ge, diamonds and diamond-like carbon coatings, or compound semiconductors of Group II-V, II-VI and other semiconductors including sulfides, selenides, tellurides, nitrides, carbides, nitrides, antimonides, and phosphides. The active layer may also comprise a metal such as tungsten or other metal which is catalytically active and interferes with light absorption, and which is capable of promoting or enhancing light energy transfer to an analyte, e.g., to ionize and desorb it from the surface of the supporting substrate. The metal may be selected from the group comprising transition metals including Fe, Co, Cr, Ni, Mo, W, V, Cu, Zn and precise metals including Ag, Au, Pt, Pd, Ru, Rh, or metal alloys thereof.

In another aspect of the invention, a mass spectrometry device is disclosed which comprises a supporting substrate having a first surface and a thin non-silicon film layer of a first material deposited on at least a region of the first surface, the film layer having a nanostructured surface; an active layer of a second material deposited on the first layer; and at least a first analyte positioned in contact with at least a region of the active layer, wherein the active layer assists in incorporating and transferring energy to the at least first analyte when irradiated with a laser during laser desorption of the analyte. The non-silicon film layer can be deposited on the substrate using a variety of well-known techniques such as thermal evaporation and sputtering including physical vapor deposition (PVD), sputter deposition, low or high temperature chemical vapor deposition (CVD), metallorganic CVD, plasma-enhanced CVD, laser ablation, or using solution deposition methods such as spray coating, dip coating, or spin coating etc. Ultra-thin metal films (e.g., films less than about 5 nm in thickness) may be deposited by atomic layer deposition (ALD) techniques. The thin film may be configured to have a nanostructured surface by, for example, simply exposing the film to hot water or water vapor. For this purpose, the thin film surface is exposed to hot water or water vapor at a temperature greater than about 50 degrees Celsius, e.g., between about 50 to 150 degrees Celsius. The water or the water vapor preferably has a temperature of from about 90 to 125 degrees Celsius. The film surface is exposed to the water or water vapor for a sufficient time (e.g., between about 3 to 60 minutes, for example, between about 5 and 30 minutes) to convert the film into a highly ordered nanostructured surface. In one embodiment, the thin film is a metal thin film made from alumina or aluminum. Other textured surfaces can also be used as long as such surfaces enhance desorption sensitivity, including, for example, a native oxide layer or a deposited oxide or nitride layer or materials including ZnO, $SiO_2$, $ZrO_2$, $HfO_2$, a hydrous form of these oxides, a compound oxide such as $SiTiO_3$, $BaTiO_3$ $PbZrO_4$ or a silicate. In other embodiments, the supporting substrate itself is made from a non-silicon material such as alumina or aluminum from which a nanostructured surface can be formed, and the active layer is deposited on the nanostructured surface of the substrate.

The active layer may comprise a semiconductor material such as silicon or germanium, or other conducting or semiconducting materials, such as metals and semimetals, and other materials which absorb light and promote or enhance light energy transfer to an analyte to ionize and desorb it from the surface of the supporting substrate as described above and further below. In one example, the active layer is made from silicon, and the silicon active layer is deposited on the thin film layer by a chemical vapor deposition process for ten or more minutes to a depth of about 50 nm or more, or by other thermal evaporation method such as sputtering. The active layer can also optionally be coated or functionalized, e.g., to enhance or add specific properties. For example, polymers, ceramics, or small molecules can optionally be used as coating materials. The optional coatings can impart characteristics such as water resistance, improved mechanical, optical (e.g., enhancement of light coupling) or electrical properties or specificities for certain analytes. The active layer may also be derivatized with one or more functional moieties to enhance laser desorption such as one or more silane groups, e.g., one or more per-fluorinated silane groups, or other coatings such as diamond-like carbon thin film coatings (e.g., to render the surface of the film hydrophobic).

The supporting substrate may be made from any one of a number of conventional materials including stainless steel, glass, quartz, semiconductor materials such as silicon, polymers, ceramics etc. Samples of the substances (e.g., small molecules, proteins, peptides etc.) to be analyzed are optionally placed in contact with the active layer (e.g., directly or via the use or one or more functional moieties such as one or more silane groups) by conventional dispensing means such as pipetting, dot-printing etc. Those of skill in the art will be familiar with various protocols to follow to dry the samples for analysis. Laser energy levels and pulse durations are also optionally optimized for analysis of the samples arrayed upon the nanostructured substrate surface. Again, those of skill in the art will be familiar with ways of determining optimal parameters for laser energy, pulse time, etc. for mass spectrometry. For example, the different parameters are optionally modified depending upon, e.g., the specific molecules being detected. For example, the laser energy used can optionally be adjusted (e.g., higher laser energy levels for peptides as opposed to small molecules).

In another embodiment of the invention, a mass spectrometry system is disclosed which generally comprises a substrate comprising a first surface and a thin non-silicon film layer of a first material (e.g., a metal such as alumina or aluminum) on at least a region of the first surface, the film having a nanostructured surface; an active layer of a second material deposited on the first layer; at least a first analyte positioned in contact with a first region of the active layer; a laser positioned to direct energy at the at least first region to desorb the at least first analyte from the first region; and a mass spectrometer instrument positioned to receive the at least first analyte desorbed from the active layer, wherein the active layer assists in incorporating and transferring energy to the at least first analyte during laser desorption. The active layer may be functionalized or coated with one or more functional moieties to enhance or add specific properties, e.g., to render its surface hydrophobic.

In other aspects of the present invention, methods are provided for manufacturing substrates for various applications including mass spectrometry, as well as methods for detecting one or more analytes, e.g., for mass spectrometry analysis, using such substrates. In one embodiment, a method for manufacturing a substrate device is disclosed which comprises providing a supporting substrate having a first surface; depositing a non-silicon film layer on the first surface; forming a nanostructured surface from the non-silicon film layer; depositing an active layer on the nanostructured surface; and depositing one or more analytes onto one or more regions of the active layer. The step of depositing a non-silicon film layer on the first surface of the substrate can comprise, for example, sputtering the film onto the first surface or using a CVD method to deposit the film on the surface of the substrate. The non-silicon film can comprise, for example, an alumina or aluminum film from which a nanostructured film surface may be easily formed, or other similar nanostructured surface. The step of forming the nanostructured surface from the film layer can comprise, for example, exposing the film layer to hot water or water vapor at a temperature of greater than about 50 degrees Celsius, e.g., between about 50 to 150 degrees Celsius, for example, between about 90 to 125 degrees Celsius, for between about three to sixty minutes, to form a highly structured surface. The step of depositing the active layer on the non-silicon film layer can comprise, for example, using a chemical vapor deposition process to deposit such film, wherein such film comprises a silicon or tungsten film in exemplary embodiments. In this way, substrates useful for a variety of applications such as mass spectrometry can be reproducibly produced easily and with relatively little cost, e.g., as compared to wet electrochemically etched porous silicon films. The method may further comprise derivatizing the active layer with one or more functional moieties to, e.g., increase the hydrophobicity of the surface and/or to assist in desorbing the one or more analytes from the surface of the active layer.

In a related aspect of the invention, a method for analyzing one or more analytes is provided which generally comprises providing a supporting substrate having a first surface and a thin non-silicon film layer deposited on the first surface and an active layer deposited on the thin film layer, the thin film layer having a nanostructured surface; and analyzing one or more analytes associated with the active layer by one or more detection means such as mass spectrometry analysis. In particular, a method for performing mass spectrometry is disclosed which comprises providing a substrate having a first surface and a thin film layer (e.g., a non-silicon layer such as alumina or aluminum) deposited on the first surface and an active layer deposited on the thin film layer, the thin film layer having a nanostructured surface and one or more analytes associated with the surface; desorbing the one or more analytes from the surface with energy from a laser directed at the surface; and analyzing the one or more analytes in a mass spectrometer instrument. The analytes to be measured include, for example, proteins, peptides, carbohydrates, fatty acids, small molecules, nucleic acids, cells, polypeptides and mixtures thereof. The analytes may be directly applied to the surface of the substrate in solid, dried form or in liquid form and dried on the substrate. The analytes may be suspended in aqueous or organic solutions or suspensions.

In another aspect of the present invention, a mass spectrometry device is disclosed which comprises a supporting substrate having a first surface and a plurality of nanocrystals, e.g., semiconductor nanocrystals such as quantum dots, deposited on the surface of the substrate. For example, the nanocrystals can be a gold nanoparticle, a cobalt nanoparticle, an iron oxide nanoparticle, or a semiconductor nanocrystal including a semiconductor material, such as a Group IV compound (e.g., Si, Ge), a Group II-VI compound, a Group II-V compound, a Group III-VI compound, a Group III-V compound, a Group IV-VI compound, a Group I-III-VI compound, a Group II-IV-VI compound, or a Group II-IV-V compound. The semiconductor material can be, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. The nanoparticle can be coated with one or more second materials such as a second metal, semimetal, polymer, or semiconductor material such as ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

In another aspect of the invention, a device for enhanced surface area and/or hydrophobic surface applications other than mass spectrometry (e.g., such as for use in medical device applications, building materials, barrier layers for storage tanks, a surface for cell attachment, differentiation and proliferation, contact touch screens for use with ATM machines, in car displays, in entertainment portals, etc.) is disclosed which generally comprises a supporting substrate having a surface, a non-silicon film layer on at least a region of the surface, the film layer having a nanostructured surface, and a hydrophobic (or hydrophilic) coating deposited on the film layer. The hydrophobic coating may comprise, for example, a diamond-like carbon coating or other coating which renders the surface of the substrate hydrophobic (or hydrophilic). The diamond-like carbon film can be applied to the nanostructured surface by, e.g., using pulsed laser ablation on a graphite target or a plasma assisted CVD method at low temperature. When the deposited material is heated, such films lose their stress, yet retain their diamond-like properties.

BRIEF DESCRIPTION OF THE DRAWINGS

FIG. 5A shows results of mass spectrometry analysis of samples on a stainless steel substrate without any nanostructured thin film layer.

FIG. 5B shows results of mass spectrometry analysis of samples on a stainless steel substrate with a silicon layer and without any underlying nanostructured thin film layer.

FIG. 5C shows results of mass spectrometry analysis of samples on a stainless steel substrate with a thin nanostructured film layer and a silicon active layer according to the teachings of the present invention

DETAILED DESCRIPTION OF THE INVENTION

The present invention describes apparatus and methods of use of a nanostructured non-silicon thin film (such as an alumina or aluminum thin film) on a supporting substrate which is subsequently coated with an active material layer. The base non-silicon material generates enhanced surface area and the appropriate structural dimensions while the active layer assists in incorporating and transferring energy to one or more analytes adsorbed on the active layer when irradiated with a laser during laser desorption of the analyte(s). In the following description numerous specific details are set forth in order to provide a thorough understanding of the present invention. One skilled in the art will appreciate that these specific details are not necessary in order to practice the present invention. In other instances, well known equipment features and processes have not been set forth in detail in order to avoid obscuring the present invention.

Figure 1:
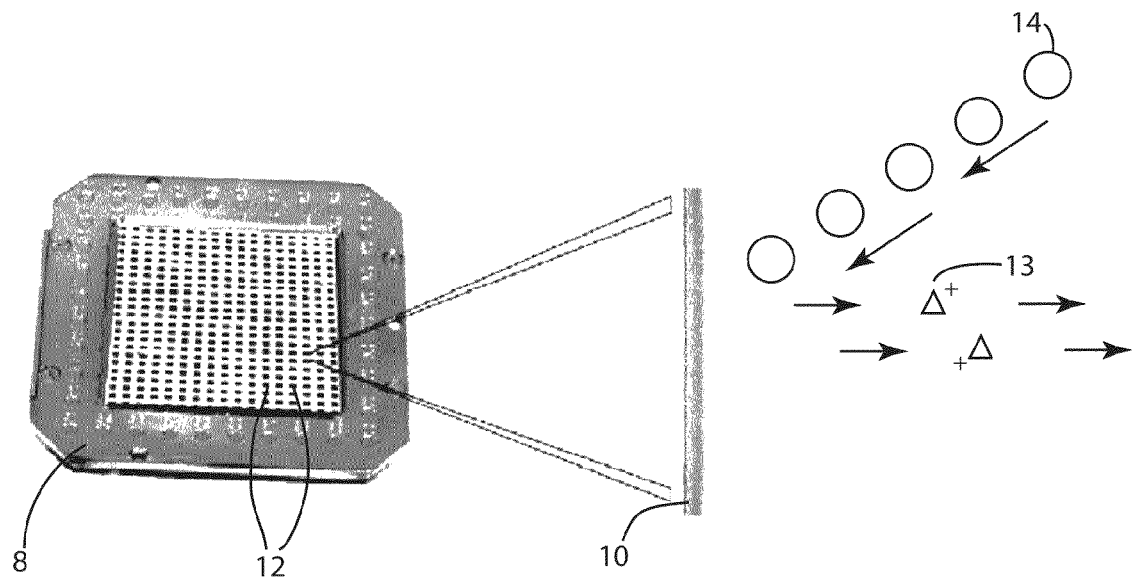
FIG. 1 shows a configuration of an exemplary laser desorption/ionization mass spectrometry setup.

FIG. 1 depicts a schematic configuration of an exemplary laser desorption/ionization mass spectrometry set-up showing a MALDI plate 8 customarily used in MALDI studies holding modified supporting substrate 10 illuminated by a series of laser pulses 14. The supporting substrate 10 can have a plurality of analytes 12 (e.g., proteins, peptides, small molecules etc.) adsorbed to it, preferably without the use of a matrix material used in conventional MALDI analyses. The modified surface of the substrate absorbs the laser pulses 14 and ionizes and releases the analytes to form a desorbed and ionized analytes 13. The desorbed and ionized analytes 13 then travel to a mass spectrometry instrument (not shown) for analysis.

Figure 2A:
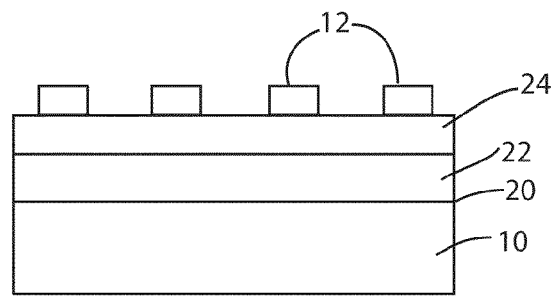
FIG. 2A is a cross-sectional view of a mass spectrometry substrate according to the teachings of the present invention.
Figure 2B:
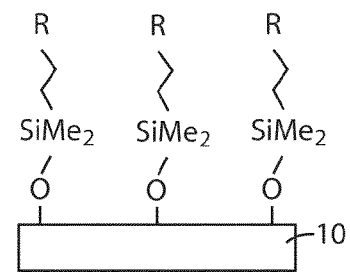
FIG. 2B is an illustration of the substrate of FIG. 2A derivatized with functionalities by silylation.

FIG. 2A shows an enlarged cross-sectional view of the modified supporting substrate 10 according to the teachings of the present invention. The supporting substrate can take a variety of forms such as a semiconductor wafer, a sheet of glass or quartz, a sheet of metal, a piece of ceramic or plastic, and the like. As shown, the supporting substrate 10 has a first surface 20 and a thin non-silicon film layer 22 of a first material deposited on at least a region of the first surface, the film layer having a nanostructured surface. An active layer 24 of a second material is deposited on the first layer. A plurality of analytes 12 are positioned in contact with at least a region of the active layer 22, either directly or via the use of one or more functional groups as shown in FIG. 2B. Without being bound to any particular theory of operation, it is believed that the active layer assists in incorporating and transferring energy (e.g., light energy from the laser pulses) to the analytes when irradiated with a laser during laser desorption of the analyte. For example, it is believed that the analyte molecules are ionized by acid-base proton transfer reactions with the protonated active layer ions in a dense phase just above the surface of the active layer. The protonated active layer molecules are generated by a series of photochemical reactions.

In one aspect of the invention, the first non-silicon layer may comprise an insulating inorganic material such as a native oxide layer or a deposited oxide or nitride layer. The insulating inorganic material may also be formed form a deposited metal layer. For example, the insulating inorganic material may be selected from the group of materials including aluminum (Al), alumina ($Al_2O_3$), ZnO, $SiO_2$, $ZrO_2$, $HfO_2$, a hydrous form of these oxides, a compound oxide such as $SiTiO_3$, $BaTiO_3$ $PbZrO_4$ or a silicate. In one example, the non-silicon film layer is made from alumina or aluminum which can be deposited on the substrate using a variety of well-known techniques such as thermal evaporation and sputtering including physical vapor deposition (PVD), sputter deposition, chemical vapor deposition (CVD), metalloorganic CVD, plasma-enhanced CVD, laser ablation, or solution deposition methods such as spray coating, dip coating, or spin coating etc. Ultra-thin metal films (e.g., films less than about 5 nm in thickness) may be deposited by atomic layer deposition (ALD) techniques. The thin film preferably has a thickness less than about 1000 nm, for example, between about 5 and 400 nm, for example, between about 5 and 200 nm, for example, between about 10 and 100 nm. When an aluminum substrate is used, the thickness of the substrate may be significantly greater, e.g., on the order of about 0.5 mm or thicker.

Figure 3:
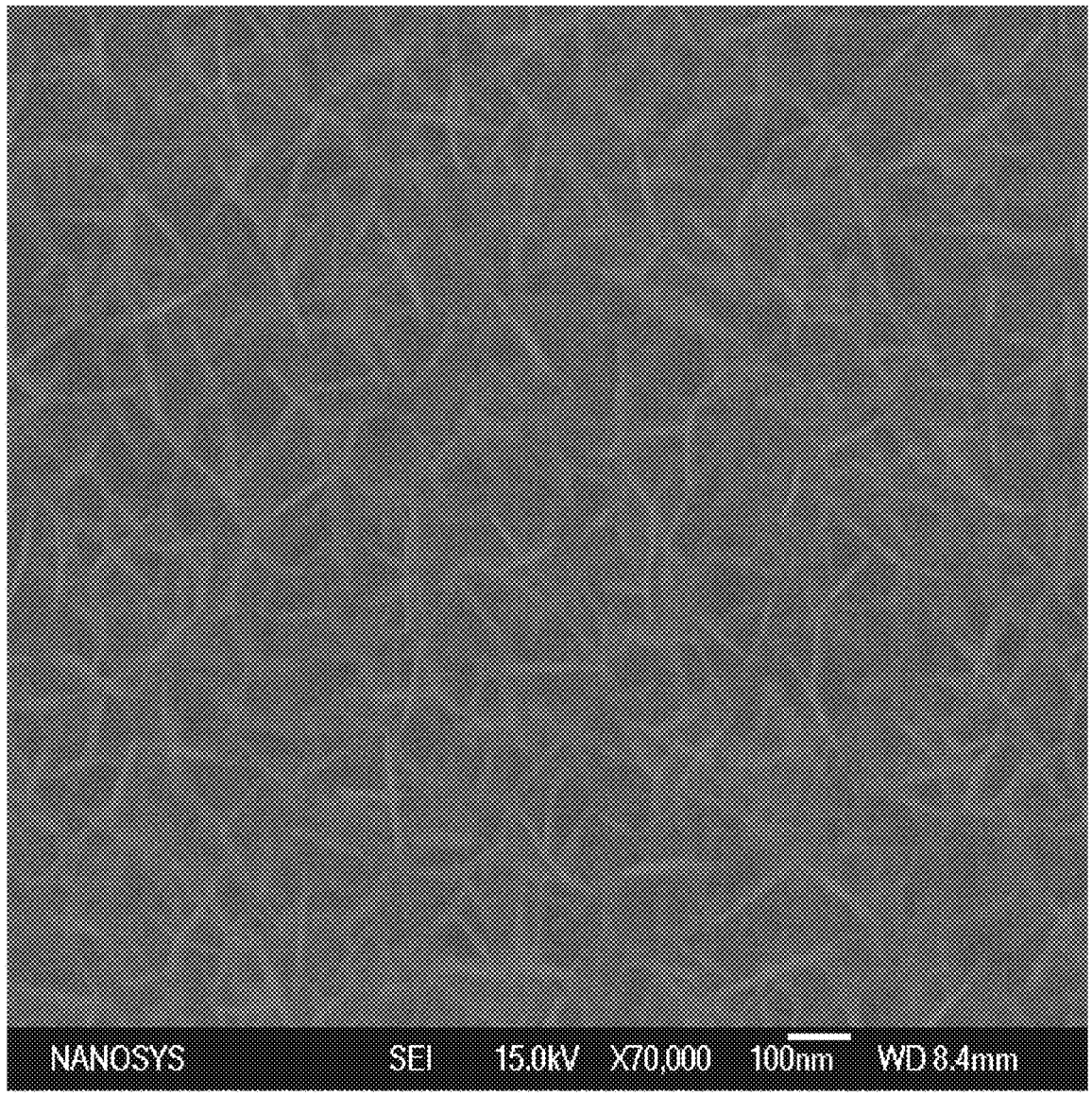
FIG. 3 shows an SEM close-up image of a nanostructured alumina film on a stainless steel substrate.
Figure 4A:
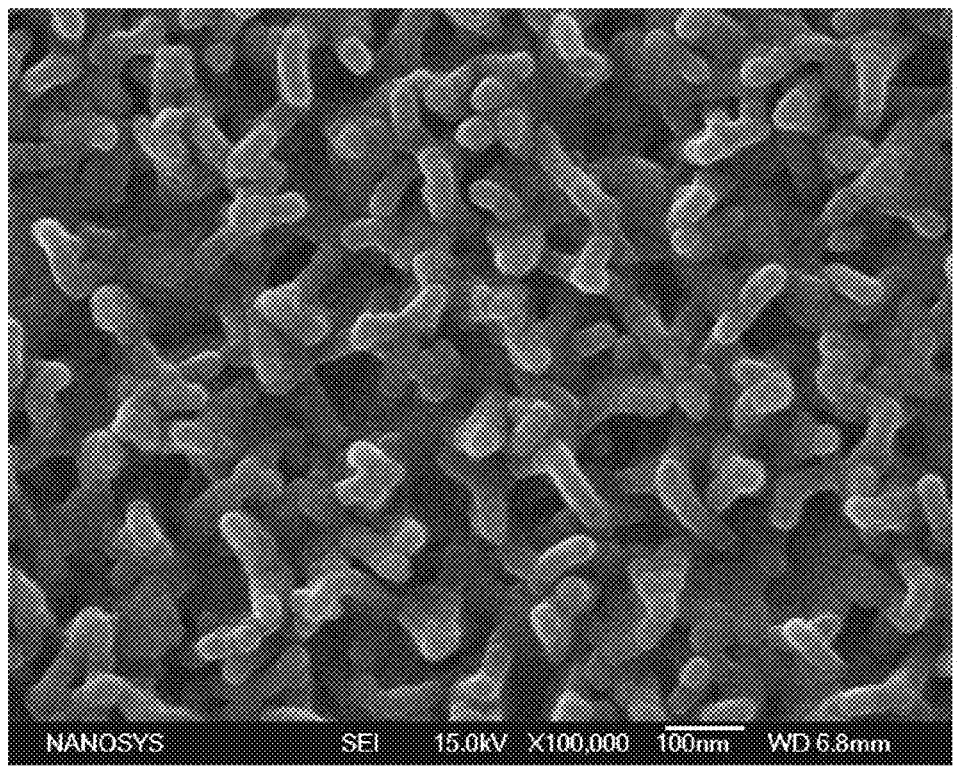
FIG. 4A shows an electron micrograph of a substrate having a nanostructured alumina surface with an active silicon layer deposited thereon.
Figure 4B:
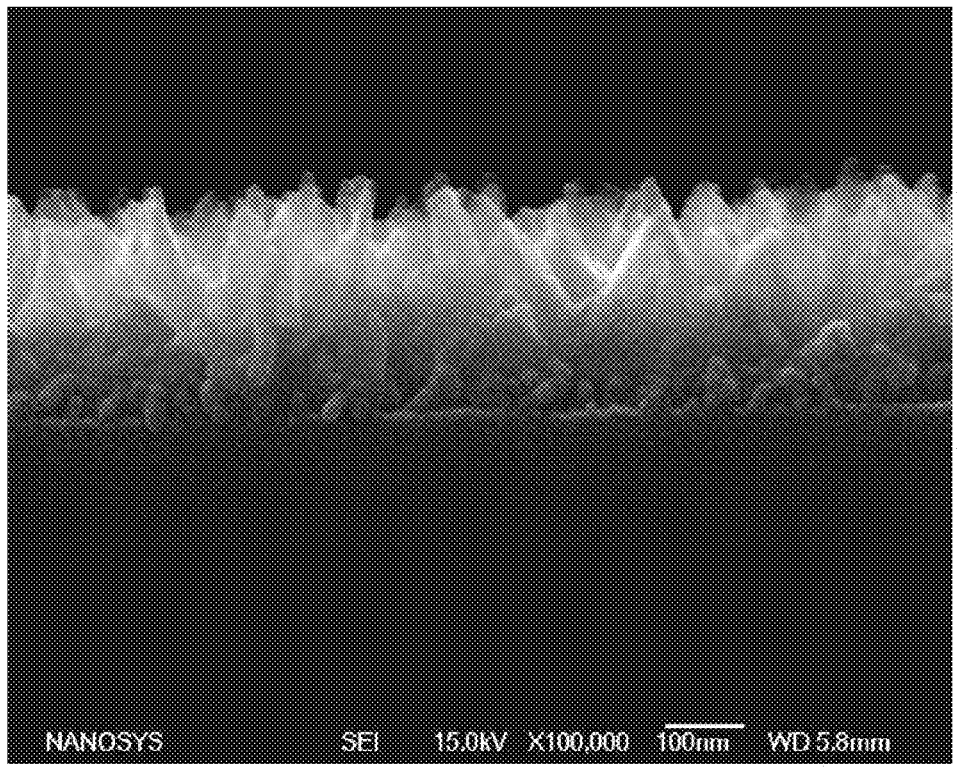
FIG. 4B is a cross-sectional electron micrograph view of the substrate surface of FIG. 4A.
Figure 6A:
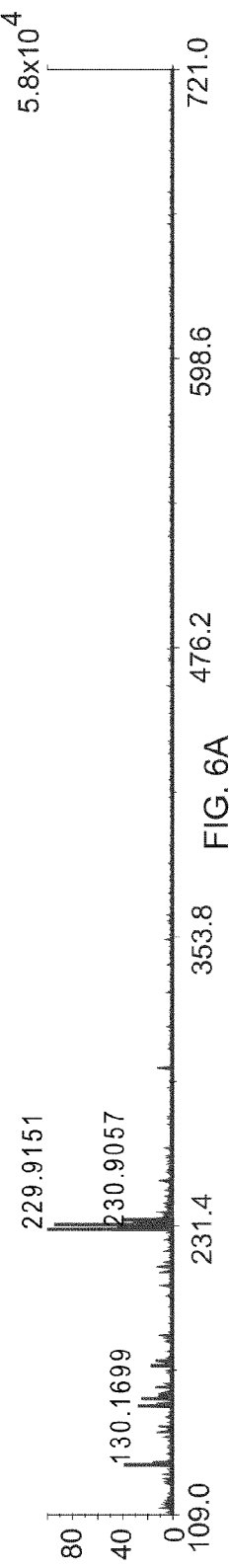
FIG. 6A shows results of mass spectrometry analysis of 25 pg of clonidine deposited on a silicon coated nanostructured alumina surface.
Figure 6B:
FIG. 6B shows results of mass spectrometry analysis of 25 pg of haloperidol deposited on a silicon coated nanostructured alumina surface.
Figure 6C:
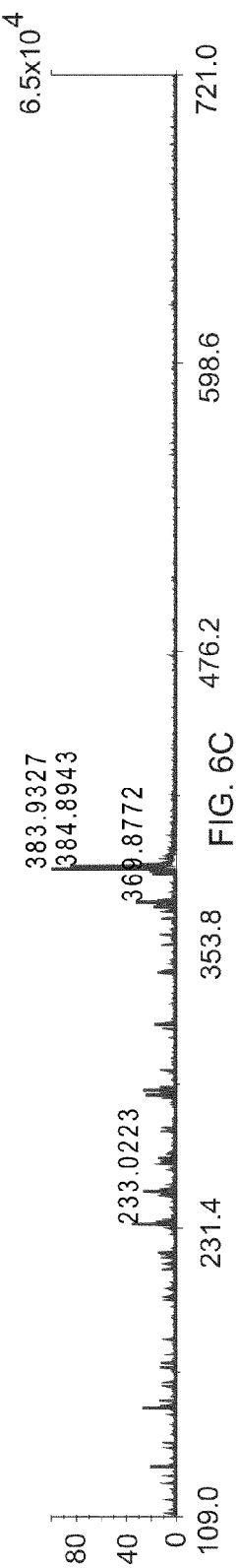
FIG. 6C shows results of mass spectrometry analysis of 25 pg of prazosin deposited on a silicon coated nanostructured alumina surface.
Figure 6D:
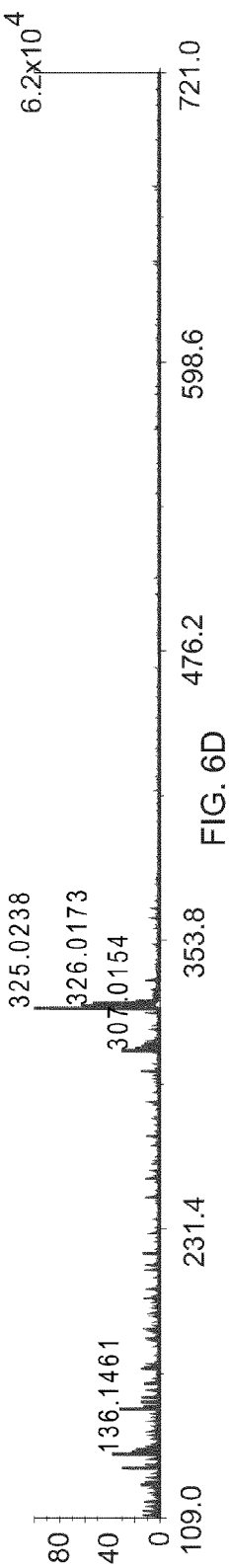
FIG. 6D shows results of mass spectrometry analysis of 25 pg of quinidine deposited on a silicon coated nanostructured alumina surface.
Figure 7A:
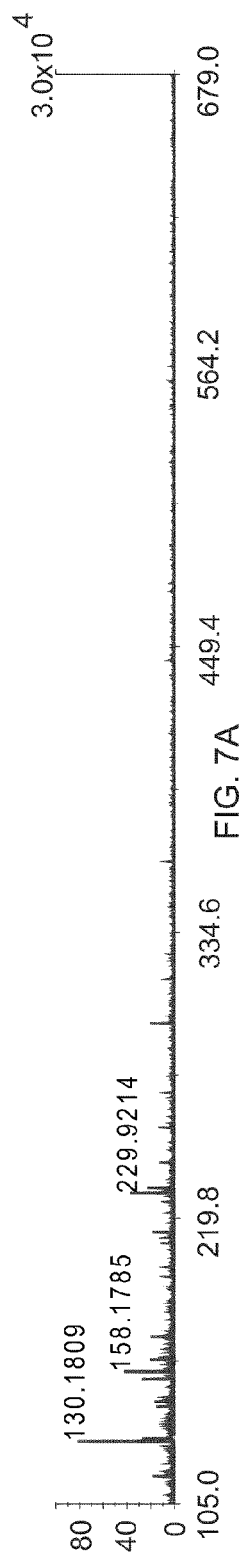
FIG. 7A shows results of mass spectrometry analysis of 2.5 pg of clonidine deposited on a silicon coated nanostructured alumina surface.
Figure 7B:
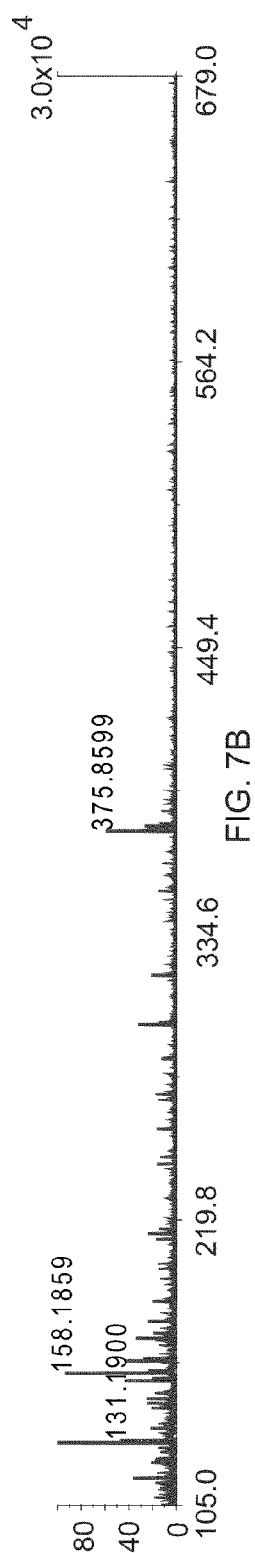
FIG. 7B shows results of mass spectrometry analysis of 2.5 pg of haloperidol deposited on a silicon coated nanostructured alumina surface.
Figure 7C:
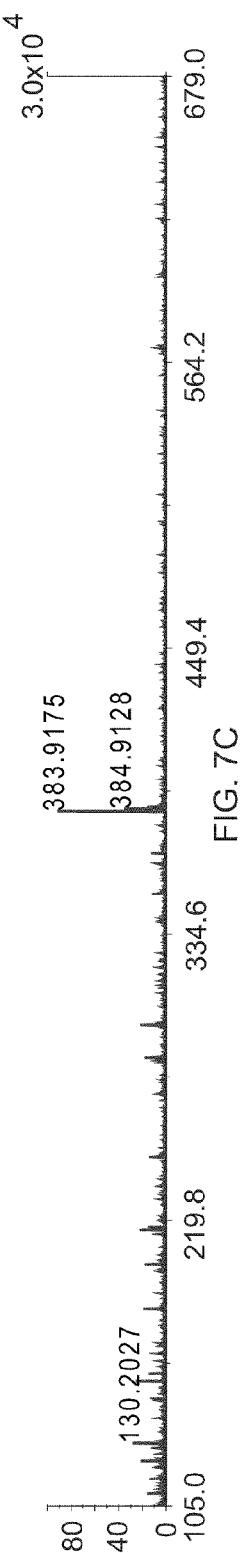
FIG. 7C shows results of mass spectrometry analysis of 2.5 pg of prazosin deposited on a silicon coated nanostructured alumina surface.
Figure 7D:
FIG. 7D shows results of mass spectrometry analysis of 2.5 pg of quinidine deposited on a silicon coated nanostructured alumina surface.
Figure 8A:
FIG. 8A shows results of mass spectrometry analysis of 25 pg of clonidine deposited on a silicon coated nanostructured aluminum substrate surface.
Figure 8B:
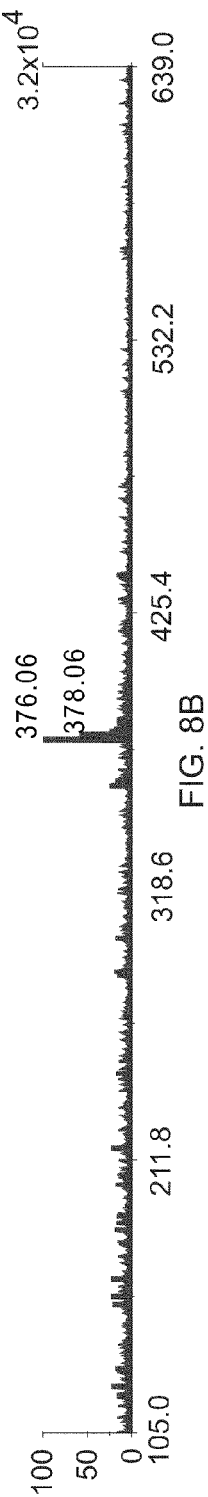
FIG. 8B shows results of mass spectrometry analysis of 25 pg of haloperidol deposited on a silicon coated nanostructured aluminum substrate surface.
Figure 8C:
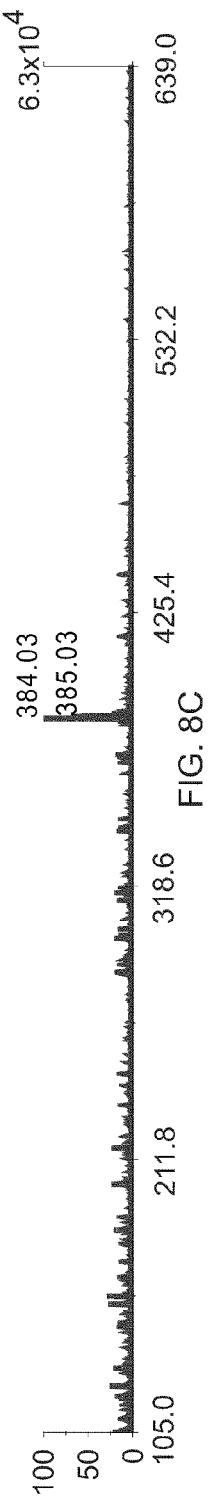
FIG. 8C shows results of mass spectrometry analysis of 25 pg of prazosin deposited on a silicon coated nanostructured aluminum substrate surface.
Figure 8D:
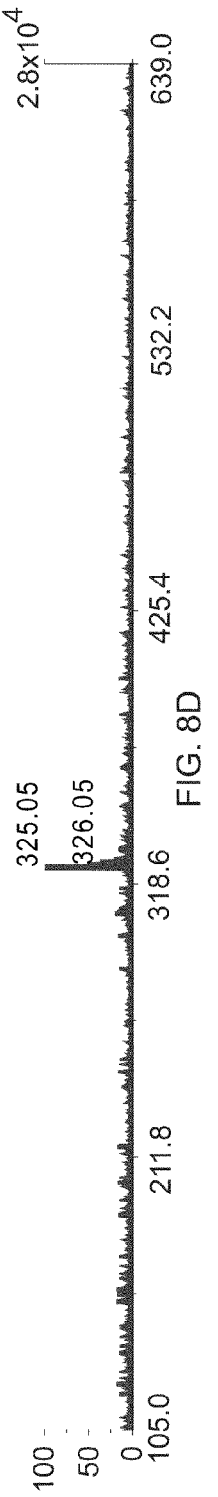
FIG. 8D shows results of mass spectrometry analysis of 25 pg of quinidine deposited on a silicon coated nanostructured aluminum substrate surface.

The inventors of the instant claimed invention have surprisingly discovered that the film layer may be configured to have a nanostructured surface as shown, for example, in the SEM images of FIGS. 3 and 4, by, for example, simply exposing the film to hot water or water vapor. For this purpose, the surface is exposed to hot water or water vapor at a temperature greater than about 50 degrees Celsius, e.g., between about 50 to 150 degrees Celsius. The water or the water vapor preferably has a temperature of from about 90 to 125 degrees Celsius. The surface is likewise preferably exposed to the water or water vapor for a sufficient time (e.g., between about 3 to 60 minutes, for example, between about 5 to 30 minutes) to convert the film into a highly ordered nanostructured surface having pore sizes less than about 200 nm. For example, FIGS. 4A-B are electron micrographs of a nanostructured alumina surface with an active silicon layer deposited thereon. As shown, the nanostructured alumina layer comprises elongated or plate-like grains with at least one dimension less than about 0.2 μm. The long axis of the plate-like grains are oriented substantially perpendicular to the surface of the supporting substrate.

The nanostructured alumina layer can also be formed by other means such as the formation of porous alumina films via the anodization of aluminum metal in acidic solution (e.g., phosphoric, oxalic, or sulfuric acid solutions), autoclaving the film layer e.g., by placing the substrate in a commercially available gravity or vacuum autoclave device, and the like. See, e.g., Evelina Palibroda, A. Lupsan, Stela Pruneanu, M. Savos, *Thin Solid Films,* 256, 101 (1995), the entire contents of which are incorporated by reference herein. Other textured surfaces other than alumina or aluminum can also be used as long as such surfaces enhance desorption sensitivity, including, for example, zinc oxide (ZnO) nanostructured surfaces described above. Low-temperature solution-based approaches to forming ZnO nanotextured surfaces are described, for example, in "Low Temperature Wafer-Scale Production of ZnO Nanowire Arrays," Lori E. Greene et al., *Angew. Chem. Int. Ed.* 2003, 42, 3031-3034, the entire contents of which are incorporated by reference herein.

The supporting substrate 10 may be made from a non-silicon material such as aluminum from which a nanostructured surface can be formed (e.g., by heating the material with water or water vapor at a temperature greater than about 50 degrees Celsius, e.g., between about 50 to 150 degrees Celsius, e.g., at a temperature of from about 90 to 125 degrees Celsius, for a period of time sufficient to form the nanostructured surface, e.g., between about 3 and 60 minutes, e.g., preferably greater than about 5 minutes), and the active layer is deposited on the nanostructured surface of the substrate. For example, FIGS. 8A-D show mass spectrometry analysis of 25 picograms of four pharmaceutical compounds (e.g., clonidine, haloperidol, prazosin, and quinidine, respectively) deposited on a silicon coated nanostructured aluminum substrate surface.

The active layer 24 on top of the nanostructured film layer may comprise a semiconductor which absorbs light energy such as IR, red, green, blue and/or UV laser light energy. The semiconductor may be selected from Group IV semiconductors including Si, Ge, diamonds and diamond-like carbon coatings, or compound semiconductors of Group II-V, II-VI and other semiconductors including sulfides, selenides, tellurides, nitrides, carbides, nitrides, antimonides, and phosphides. The active layer may also comprise a metal such as tungsten (W) or other metal which is catalytically active and that interferes with light absorption, and which is capable of promoting or enhancing light energy transfer to an analyte, e.g., to ionize and desorb it from the surface of the supporting substrate. The metal may be selected from the group comprising transition metals including Fe, Co, Cr, Ni, Mo, W, V, Cu, Zn and precise metals including Ag, Au, Pt, Pd, Ru, Rh, or metal alloys thereof.

Figure 9A:
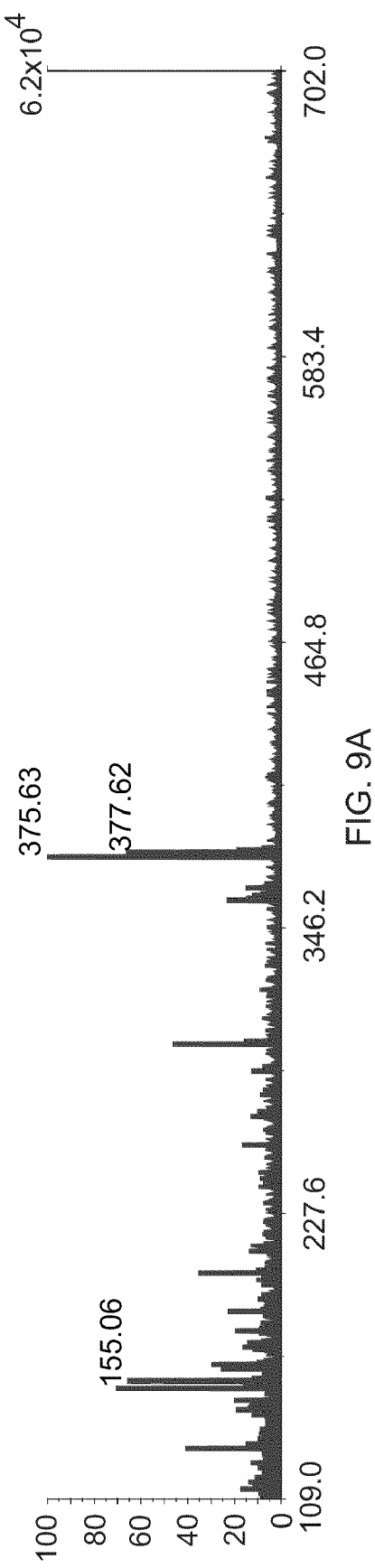
FIG. 9A shows results of mass spectrometry analysis of 25 pg of haloperidol deposited on a silicon coated nanostructured alumina surface that had the silicon active layer deposited by CVD for a deposition time of about 30 minutes.
Figure 9B:
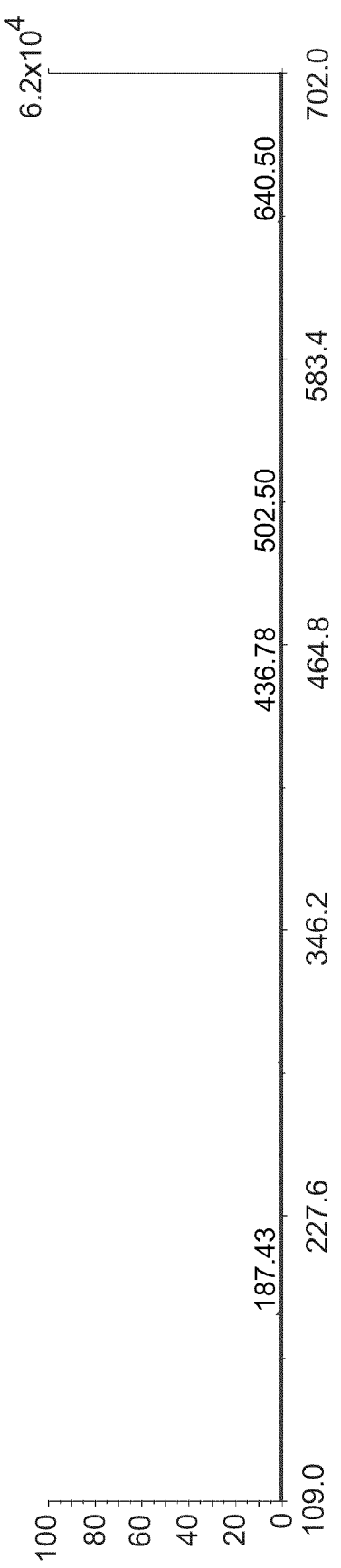
FIG. 9B shows results of mass spectrometry analysis of 25 pg of haloperidol deposited on a silicon coated nanostructured alumina surface that had the silicon active layer deposited by CVD for a deposition time of about 10 minutes.
Figure 10A:
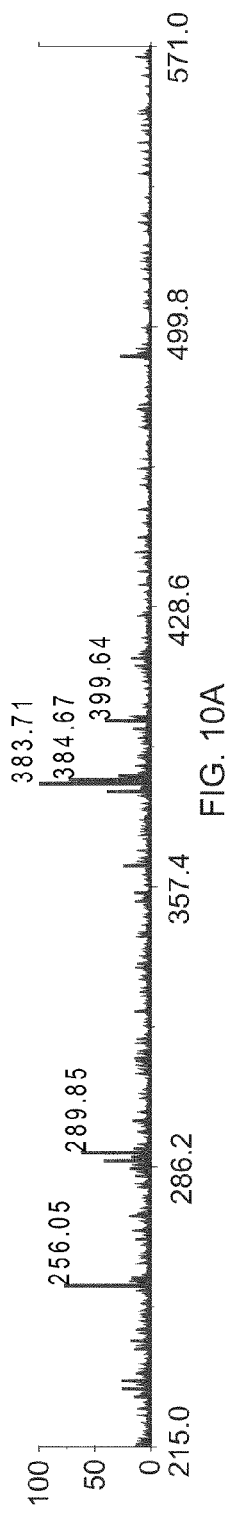
FIG. 10A shows results of mass spectrometry analysis of 25 pg of prazosin deposited on a tungsten coated nanostructured aluminum substrate surface.
Figure 10B:
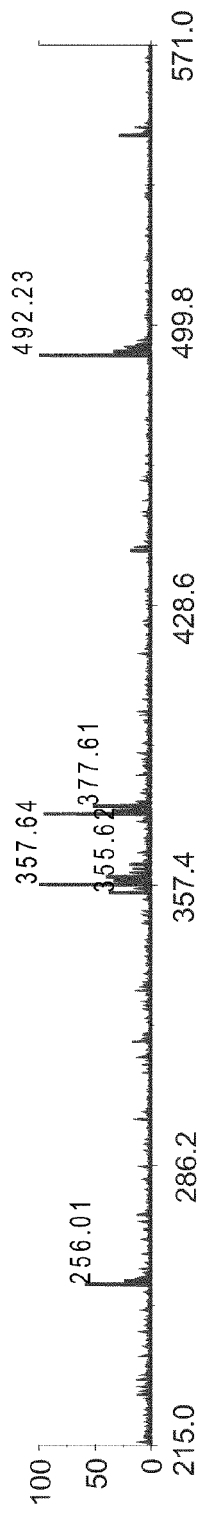
FIG. 10B shows results of mass spectrometry analysis of 25 pg of haloperidol deposited on a tungsten coated nanostructured aluminum substrate surface.
Figure 10C:
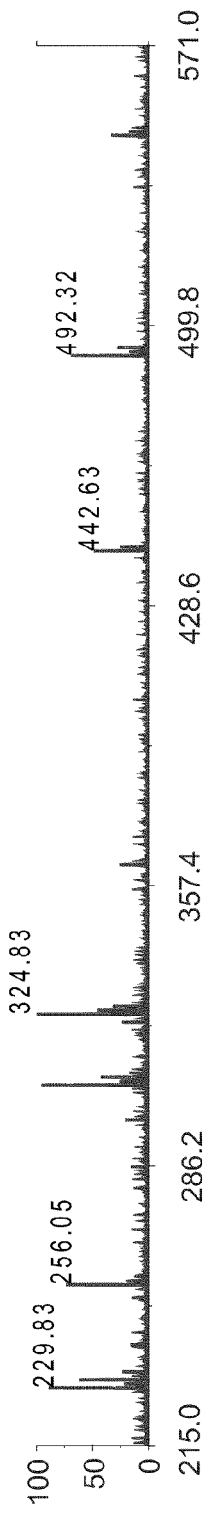
FIG. 10C shows results of mass spectrometry analysis of 25 pg of quinidine deposited on a tungsten coated nanostructured aluminum substrate surface.
Figure 10D:
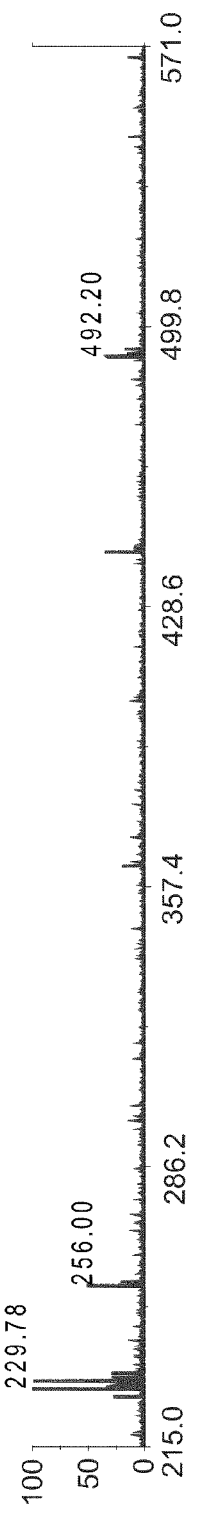
FIG. 10D shows results of mass spectrometry analysis of 25 pg of clonidine deposited on a tungsten coated nanostructured aluminum substrate surface.

The active layer preferably has a thickness of between about 5 and 200 nm, for example, between about 10 and 50 nm. When silicon is used as the active layer, the silicon active layer is deposited on the thin film layer by a chemical vapor deposition process or by other thermal evaporation method. For example, it has been shown that depositing the silicon active layer in a CVD oven at a temperature of about 480 degrees Celsius for a time period of between about 10 and 80 minutes, for example, between about 30 and 80 minutes, provides the optimum mass spectrometry results. For example, FIGS. 9A-B illustrate the difference in peak signal for mass spectrometry analysis of 25 picograms of haloperidol spotted onto a silicon coated nanostructured alumina surface that had silicon deposition times in the CVD oven of thirty minutes (FIG. 9A) and ten minutes (FIG. 9B). It will be appreciated that the haloperidol peak only appears on the silicon coated surface that was CVD deposited for about 30 minutes. Thus, the CVD deposition time (and hence silicon active layer thickness) plays an important role in the sensitivity of the mass spectrometry signal.

The active layer can also optionally be coated or functionalized, e.g., to enhance or add specific properties. For example, polymers, ceramics, or small molecules can optionally be used as coating materials. The optional coatings can impart characteristics such as water resistance, improved mechanical, optical (e.g., enhancement of light coupling) or electrical properties or specificities for certain analytes. The active layer may also be derivatized with one or more functional moieties (e.g., a chemically reactive group) to enhance laser desorption such as one or more silane groups, e.g., one or more per-fluorinated silane groups, or other coatings such as diamond coatings, a hydrocarbon molecule, a fluorocarbon molecule, or a short chain polymer of both types of molecules which may be attached to the active layer via silane chemistry. Those of skill in the art will be familiar with numerous functionalizations and functionalization techniques which are optionally used herein (e.g., similar to those used in construction of separation columns, bio-assays, etc.).

For example, details regarding relevant moiety and other chemistries, as well as methods for construction/use of such, can be found, e.g., in Hermanson *Bioconjugate Techniques* Academic Press (1996), Kirk-Othmer *Concise Encyclopedia of Chemical Technology* (1999) Fourth Edition by Grayson et al. (ed.) John Wiley & Sons, Inc., New York and in Kirk-Othmer *Encyclopedia of Chemical Technology* Fourth Edition (1998 and 2000) by Grayson et al. (ed.) Wiley Interscience (print edition)/ John Wiley & Sons, Inc. (e-format). Further relevant information can be found in *CRC Handbook of Chemistry and Physics (*2003) 83$^{rd}$ edition by CRC Press. Details on conductive and other coatings, which can also be incorporated onto the active layer of the invention by plasma methods and the like can be found in H. S. Nalwa (ed.), *Handbook of Organic Conductive Molecules and Polymers*, John Wiley & Sons 1997. See also, "ORGANIC SPECIES THAT FACILITATE CHARGE TRANSFER TO/FROM NANOCRYSTALS," US Patent Publication No. US20040178390. Details regarding organic chemistry, relevant for, e.g., coupling of additional moieties to a functionalized surface can be found, e.g., in Greene (1981) *Protective Groups in Organic Synthesis* John Wiley and Sons, New York, as well as in Schmidt (1996) *Organic Chemistry* Mosby, St Louis, Mo., and March's *Advanced Organic Chemistry Reactions, Mechanisms and Structure*, Fifth Edition (2000) Smith and March, Wiley Interscience New York ISBN 0-471-58589-0,and US Patent Publication No. US20050181195, entitled "Super-hydrophobic Surfaces, Methods of Their Construction and Uses Therefor." Those of skill in the art will be familiar with many other related references and techniques amenable for functionalization of surfaces herein. The analytes may be directly linked to the active layer surface, e.g., through silane groups, or may be coupled via linker binding groups or other appropriate chemical reactive groups to participate in linkage chemistries (derivitization) with linking agents such as, e.g., substituted silanes, diacetylenes, acrylates, acrylamides, vinyl, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, trichloro-perfluoro octyl silane, hydroxysuccinimides, maleimides, haloacetyls, pyridyl disulfides, hydrazines, ethyldiethylamino propylcarbodiimide, and/or the like.

The supporting substrate 10 may be made from any one of a number of conventional materials including stainless steel, glass, quartz, semiconductor materials such as a semiconductor wafer, silicon, polymers, ceramics etc. Samples of the substances (e.g., small molecules, proteins, peptides etc.) to be analyzed are optionally placed in contact with the active layer (e.g., directly or via the use or one or more functional moieties such as one or more silane groups described above) by conventional dispensing means such as pipetting, dot-printing etc. Those of skill in the art will be familiar with various protocols to follow to dry the samples for analysis. Laser energy levels and pulse durations are also optionally optimized for analysis of the samples arrayed upon the nanostructured substrate surface. Again, those of skill in the art will be familiar with ways of determining optimal parameters for laser energy, pulse time, etc. for mass spectrometry. For example, the different parameters are optionally modified depending upon, e.g., the specific molecules being detected. For example, the laser energy used can optionally be adjusted (e.g., higher laser energy levels for peptides as opposed to small molecules). An interesting feature of the nanostructured surface of the present invention is that it requires relatively low laser energy (e.g., on the order of about 60 Hz) to desorb small molecules therefore reducing background ion interference.

In another aspect of the present invention, a mass spectrometry device is disclosed (e.g., for matrix-free analysis of small molecules such as proteins, peptides, or small molecule drugs) which comprises a supporting substrate having a first surface and a plurality of nanocrystals, e.g., semiconductor nanocrystals such as quantum dots, deposited on the surface of the substrate. For example, the nanocrystals can be a gold nanoparticle, a cobalt nanoparticle, an iron oxide nanoparticle, or a semiconductor nanocrystal including a semiconductor material, such as a Group IV compound (e.g., Si, Ge), a Group II-VI compound, a Group II-V compound, a Group III-VI compound, a Group III-V compound, a Group IV-VI compound, a Group I-III-VI compound, a Group II-IV-VI compound, or a Group II-IV-V compound. The semiconductor material can be, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. The nanoparticle can be coated with one or more second materials such as a second metal, semimetal, polymer, or semiconductor material such as ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

In one embodiment, the nanoparticles are spin-coated onto the substrate surface, and then plasma treated to generate a water adsorbable oxide surface. The nanoparticles can also be spotted from solution onto the substrate surface (e.g., alone or in combination with the molecules to be sampled such as low molecular weight proteins, peptides or small molecule drugs), or can be applied to the surface by any other suitable method known to those of ordinary skill in the art. Alternatively, the nanocrystals can be applied directly to a tissue section whereupon energy transfer occurs from the nanocrystals directly to molecules in the tissue sample (such as proteins or small molecule drugs) which would be desorbed and ionized for mass spectrometry analysis. The surface of the nanoparticles can be functionalized as necessary. In certain embodiments, the collection or population of nanocrystals is substantially monodisperse in size and/or shape. See, e.g., U.S. Pat. No. 6,207,229 (Mar. 27, 2001) and U.S. Pat. No. 6,322,901 (Nov. 27, 2001) to Bawendi et al. entitled "Highly luminescent color-selective materials," the entire contents of each of which are incorporated by reference herein.

While any method known to the ordinarily skilled artisan can be used to create nanocrystals suitable for use in the present invention, suitably, a solution-phase colloidal method for controlled growth of inorganic nanocrystals is used. See Alivisatos, A. P., "Semiconductor clusters, nanocrystals, and quantum dots," *Science* 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," *J. Am. Chem. Soc.* 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," *J. Am. Chem. Soc.* 115:8706 (1993). This manufacturing process technology leverages low cost processability without the need for clean rooms and expensive manufacturing equipment. In these methods, metal precursors that undergo pyrolysis at high temperature are rapidly injected into a hot solution of organic surfactant molecules. These precursors break apart at elevated temperatures and react to nucleate nanocrystals. After this initial nucleation phase, a growth phase begins by the addition of monomers to the growing crystal. The result is freestanding crystalline nanoparticles in solution that have an organic surfactant molecule coating their surface.

Utilizing this approach, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape. The ratio of surfactants to monomer, surfactants to each other, monomers to each other, and the individual concentrations of monomers strongly influence the kinetics of growth. In suitable embodiments, Si or CdSe is used as the nanocrystal material, although other suitable semiconductor materials can be used as described above (e.g., InP, ZnS, and the like).

By controlling the size and composition of the semiconductor nanocrystals used in the practice of this embodiment of the present invention, the nanocrystals will absorb laser light of a particular wavelength, or a particular range of wavelengths, whereupon efficient energy transfer from the nanocrystal to the molecules deposited thereon or therewith can occur to desorb and ionize the molecules for mass spectrometry analysis. The ability to make nanocrystals out of different semiconductors, and to control their size and shape, allows for the fabrication of nanocrystals that will absorb light from the UV, to visible, to near infrared (NIR), to infrared (IR) wavelengths. Nanocrystals for use in the present invention will suitably be less than about 100 nm in size, and down to less than about 2 nm in size. In suitable embodiments, the nanocrystals of the present invention absorb ultraviolet light, e.g., at a wavelength of between about 300 and 400 nm.

In another aspect of the invention, a device for enhanced surface area applications and/or hydrophobic surface applications is disclosed which generally comprises a supporting substrate, a non-silicon film layer on at least a region of the surface, the film layer having a nanostructured surface, and a hydrophobic (or hydrophilic) coating deposited on the film layer. The hydrophobic coating may comprise, for example, a diamond-like carbon coating (e.g., an amorphous diamond film) or other coating which renders the surface of the device hydrophobic (or hydrophilic). The diamond-like carbon film can be applied to the nanostructured surface by, e.g., using pulsed laser ablation on a graphite target or by a plasma assisted CVD method at low temperature. When the deposited material is heated, such films lose their stress, yet retain their diamond-like properties.

Such devices can be used in a variety of high surface area and/or hydrophobic or hydrophilic surface applications including those which are disclosed in greater detail in co-pending and related cases U.S. Pat. No. 7,074,294, which is a continuation-in-part of U.S. Pat. No. 7,056,409, which claims priority to U.S. Provisional Patent Application No. 60/463,766, filed Apr. 17, 2003; and U.S. patent application Ser. No. 10/833,944, filed Apr. 27, 2004, which claims priority to U.S. Provisional Application Ser. No. 60/466,229, filed Apr. 28, 2003; and to U.S. patent application Ser. No. 10/840,794 filed May 5, 2004, which is a continuation-in-part of U.S. patent application Ser. No. 10/792,402, filed Mar. 2, 2004, which claims priority to U.S. Provisional Patent Application Ser. Nos. 60/468,390, filed May 6, 2003 and 60/468,606 filed May 5, 2003, each of which has previously been incorporated by reference in their entirety herein.

For example, as disclosed in the above-referenced applications, the unique nanostructured surfaces disclosed herein can be used in, on or within various medical devices, such as clamps, valves, intracorporeal or extracorporeal devices (e.g., catheters), temporary or permanent implants, stents, vascular grafts, anastomotic devices, aneurysm repair devices, embolic devices, implantable devices (e.g., orthopedic implants) and the like. Such enhanced surfaces provide many enhanced attributes to the medical devices in, on, or within which they are used including, e.g., to prevent/reduce bio-fouling, increase fluid flow due to hydrophobicity, increase adhesion, biointegration, etc. Such nanostructured coatings can be used as surface coatings for touch screens such as for information kiosks, gaming/entertainment/media consoles, point-of-sale terminals, industrial and medical instrumentation, ATM machines, kiosks in retailing, personal computer monitor screens, automobile displays, and the like. The nanostructured films disclosed herein can be used to provide a surface for cell attachment, differentiation, and proliferation, as a substrate to promote cell growth, or as a substrate for DNA or protein microarrays, e.g., to hybridize nucleic acids, proteins and the like. The nanostructured films disclosed herein have applications in vivo for tissue grafting including osteoblasts, neuronal, glia, epidermal, fibroblast cells and the like. Such nanostructured coatings can also be combined in particular applications with other nanostructured components such as nanofibers or nanowires which can be grown on the surfaces and/or deposited thereon, to provide further attributes of increased adhesion, hydrophobicity, hydropholicity, conductivity (e.g., for electrical contact applications) and the like to the devices with which they are used.

EXAMPLES

Example 1

The following non-limiting example demonstrates the feasibility of using an alumina nanostructured underlying thin film coated with an active silicon layer to perform mass spectrometry analysis. The nanostructured surface used in these experiments is based on alumina. 50 nm of alumina was sputtered onto a 40 mm square polished stainless steel plate. The plate was exposed to boiling water for three minutes which converts the alumina into a highly structured surface.

The plate was then oxygen plasma cleaned for 10 minutes before placing it into a CVD furnace where silicon was deposited on it for 70 minutes. Two steel plates without the nanostructured alumina were also placed into the furnace as controls, one with no coating (FIG. 5A) and the other with a silicon film layer deposited thereon but no underlying alumina nanostructured surface (FIG. 5B). When the plates were removed from the furnace they were exposed to trichloro-perfluoro octyl silane (Gelest, Morrissville, Pa.) vapor for four hours to render them hydrophobic along with a plane steel plate. The plates were spotted with 0.5 ul of Prazosin in a 50% acetonitrile water mix, allowed to dry and then inserted into an ABI Voyager DE-pro mass spectrometer (available commercially from Applied Biosystems, Foster City, Calif.) for analysis.

FIG. 5A shows results of mass spectrometry analysis of samples on the stainless steel substrate without any nanostructured thin film layer or silicon film layer. FIG. 5B shows results of mass spectrometry analysis of samples on a stainless steel substrate with a silicon layer and without any underlying nanostructured thin film layer. FIG. 5C shows results of mass spectrometry analysis of samples on a stainless steel substrate with a thin nanostructured film layer and a silicon active layer according to the teachings of the present invention. As can be seen almost no signal can be detected on the steel or silicon treated surfaces, but with the underlying alumina nanostructured surface, the Prazosin peak is off scale representing more then a 100× improvement.

FIGS. 6A-D show further examples of mass spectrometry analysis of 25 picograms of four pharmaceutical compounds (e.g., clonidine, haloperidol, prazosin, and quinidine, respectively) deposited on a silicon coated nanostructured alumina surface. FIGS. 7A-D show examples of mass spectrometry analysis of 2.5 picograms of those same four compounds deposited on a silicon coated nanostuctured alumina surface. As can be appreciated, the mass spectra demonstrate signal detection of all four molecules spotted at 25 pg and 2.5 pg, respectively.

Example 2

The following non-limiting example demonstrates the feasibility of using an aluminum nanostructured underlying thin film coated with an active tungsten layer to perform mass spectrometry analysis. The nanostructured surface used in these experiments is based on aluminum. 100 nm of aluminum was sputtered onto a 40 mm square polished stainless steel plate. The plate was exposed to boiling water for five minutes which converts the aluminum into a highly structured surface.

The plate was then oxygen plasma cleaned for 10 minutes before placing it into a high vacuum sputtering system (UHV Sputtering Inc., San Jose, Calif.) where tungsten was deposited on it to a depth of 50 nm. The plate was then plasma cleaned again and was exposed to trichloro-perfluoro octyl silane (Gelest, Morrisville, Pa.) vapor for three hours to render it hydrophobic. The plate was then washed thoroughly in methanol and baked for 20 minutes at 100 degrees Celsius. The plate was spotted with 25 pg of prazosin, haloperidol, quinidine and clonidine in a 50% acetonitrile water mix, allowed to dry and then inserted into an ABI Voyager DE-pro mass spectrometer (available commercially from Applied Biosystems, Foster City, Calif.) for analysis.

FIGS. 10A-D show results of mass spectrometry analysis of 25 picograms of the four pharmaceutical compounds (e.g., prazosin, haloperidol, quinidine and clonidine, respectively) deposited on the tungsten coated nanostructured aluminum surface. As can be appreciated, the mass spectra demonstrate signal detection of all four molecules spotted at 25 pg.

While the foregoing is directed to preferred embodiments of the present invention, other and further embodiments of the invention may be devised without departing from the basic scope thereof, and the scope thereof is determined by the claims which follow.

What is claimed:

1. A method for manufacturing a device useful for analysis of one or more analytes comprising:
   providing a supporting substrate having a first surface and a first film layer deposited on the first surface;
   forming a nanostructured surface from the first film layer by (a) exposing the film layer to water or water vapor at a temperature of between about 90 to 100 degrees Celsius or (b) autoclaving the film layer;
   depositing a second layer comprising silicon or tungsten on the nanostructured surface; and
   depositing one or more analytes onto one or more regions of the second layer.

2. The method of claim 1, wherein the first film layer comprises alumina or aluminum.

3. The method of claim 2, wherein the second layer comprises silicon.

4. The method of claim 3, wherein the second layer is deposited on the first film layer by a chemical vapor deposition process.

5. The method of claim 4, wherein the step of forming a nanostructured surface comprises exposing the alumina or aluminum film to water or water vapor at a temperature of between about 90 to 100 degrees Celsius for between about five to thirty minutes.

6. The method of claim 5, further comprising functionalizing the surface of the second layer with one or more functional groups.

7. The method of claim 6, wherein the one or more functional groups comprise a functional organic layer comprising a hydrocarbon molecule, a fluorocarbon molecule, or a short chain polymer of both types of molecules.

8. The method of claim 7, wherein the one or more functional groups comprise a functional organic layer comprising a fluorocarbon molecule.

9. The method of claim 1, wherein said first film layer has a thickness of between about 10 nm to 1000 nm.

10. The method of claim 9, wherein said first film layer has a thickness of between about 100 nm and 200 nm.

11. The method of claim 1, wherein said second layer has a thickness between about 5 and 200 nm.

12. The method of claim 11, wherein said second layer has a thickness between about 10 and 50 nm.

* * * * *